US00PP23341P2

(12) United States Plant Patent
Ault et al.

(10) Patent No.: US PP23,341 P2
(45) Date of Patent: Jan. 22, 2013

(54) ***VERONICA* PLANT NAMED 'TIDAL POOL'**

(50) Latin Name: *Veronica* hybrid
Varietal Denomination: Tidal Pool

(75) Inventors: James Robert Ault, Libertyville, IL (US); Catherine S. Thomas, Northfield, IL (US)

(73) Assignee: Chicago Land Grows, Glencoe, IL (US)

( * ) Notice: Subject to any disclaimer, the term of this patent is extended or adjusted under 35 U.S.C. 154(b) by 0 days.

(21) Appl. No.: 13/200,430

(22) Filed: Sep. 23, 2011

(51) Int. Cl.
*A01H 5/00* (2006.01)

(52) U.S. Cl. ..... Plt./251

(58) Field of Classification Search ..... Plt./251
See application file for complete search history.

*Primary Examiner* — Annette Para
(74) *Attorney, Agent, or Firm* — Penny J. Aguirre

(57) ABSTRACT

A new cultivar of *Veronica* plant, 'Tidal Pool', that is characterized by its exhibits a vigorously growing groundcover habit, its deep blue flowers, it's adaptability to growing in clay or sandy soils, and its leaves that are obovate in shape with 4 to 8 shallow lobes, medium green in color and sparsely pubescent on upper and lower surfaces.

2 Drawing Sheets

Botanical classification: *Veronica* hybrid.
Variety denomination: 'Tidal Pool'.

BACKGROUND OF THE INVENTION

The present invention relates to a new and distinct cultivar of *Veronica* plant of hybrid origin and will be referred to hereinafter by its cultivar name, 'Tidal Pool'. The new cultivar of *Veronica* is a hardy herbaceous perennial grown for landscape use.

The new cultivar arose from a breeding program conducted by the Inventors in Glencoe, Ill. The objective was to develop an interspecific hybrid that would combine the desirable traits of both parents (attractive flowers, groundcover growth habit, drought tolerance, etc.) combined with hybrid vigor (e.g. be more vigorous than either parent) as is typical of F1 hybrids, as well as potentially be more adaptable to a clay soil than either of the parent species.

The new cultivar of *Veronica* arose from a cross made in May 2007 between an unnamed plant of *Veronica armena* as the female parent and *Veronica pectinata* 'Rosea' (not patented) as the male parent. Flowers of the seed parent were emasculated just after petal expansion but prior to anther dehiscence to prevent self-pollination and the petals were also removed to deter insect visitation to the emasculated flowers. Flowers were then hand-pollinated within 24 hours of emasculation. 'Tidal Pool' was selected as a single unique plant from the seedlings derived from the above cross in June 2008.

Asexual reproduction of the new cultivar was first accomplished by shoot tip cuttings by one of the Inventors in June 2008 in Glencoe, Ill. The characteristics of the new cultivar have been found to be stable and to reproduce true to type in successive generations.

SUMMARY OF THE INVENTION

The following traits have been repeatedly observed and represent the characteristics of the new cultivar. These attributes in combination distinguish 'Tidal Pool' as a new and unique cultivar of *Veronica*.

1. 'Tidal Pool' exhibits a vigorously growing groundcover habit, spreading at a faster rate than either of the parent plants and other *Veronica* cultivars known to the Inventor.
2. 'Tidal Pool' exhibits deep blue flowers.
3. 'Tidal Pool' is equally adaptable to growing in clay or sandy soils, most cultivars of *Veronica* known to the Inventor grow better in sandy rather than clay soils in Illinois.
4. 'Tidal Pool' exhibits leaves that are obovate in shape with 4 to 8 shallow lobes, medium green in color and sparsely pubescent on upper and lower surfaces.

The female parent, an unnamed plant of *Veronica armena*, differs from 'Tidal Pool' in having a slower rate of spread, in having flowers that are lighter blue in color, and in having leaves that are darker green in color with deeply incised lobes that are linear in shape and leaf surfaces that lack pubescence except on its margins. The male parent, *Veronica pectinata* 'Rosea', differs from 'Tidal Pool' in having a slower rate of spread, in having flowers that are rose pink to rose violet in color, and in having slightly larger leaves that are darker green in color with leave margins that are finely crenated. 'Tidal Pool' can be also compared to the cultivar *V. pectinata* 'Alba' (not patented) and a typical plant of the species *Veronica oltensis*. Both comparison plants are similar to 'Tidal Pool' in having a groundcover type habit, in blooming in late spring to early summer and then sporadically throughout the summer, and in having evergreen foliage in mild conditions. *V. pectinata* 'Alba' differs from 'Tidal Pool' in having flowers that are white in color with a small violet eye and leaves that are densely pubescent on the upper and lower surface with margins that are double lobed. A typical plant of *Veronica oltensis* differs from 'Tidal Pool' in having leaves that are smaller in size, are less pubescent with trichomes only on the upper surface and along the midvein on the lower surface, and that are lobed with a broad terminal lobe.

BRIEF DESCRIPTION OF THE DRAWINGS

The accompanying colored photographs illustrate the overall appearance and distinct characteristics of the new

*Veronica*. The photographs were taken of a plant approximately two years in age as grown outdoors in a trial bed in Glencoe, Ill.

Figure 1:
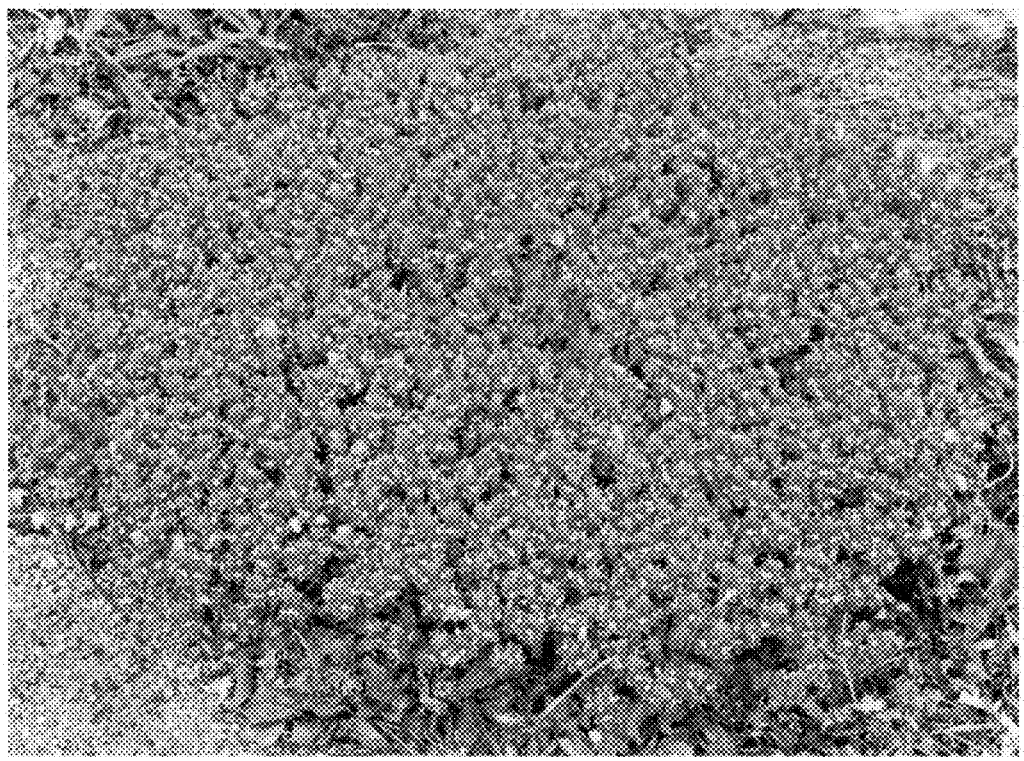

The photograph in FIG. 1 provides a top view of 'Tidal Pool' in bloom.

Figure 2:
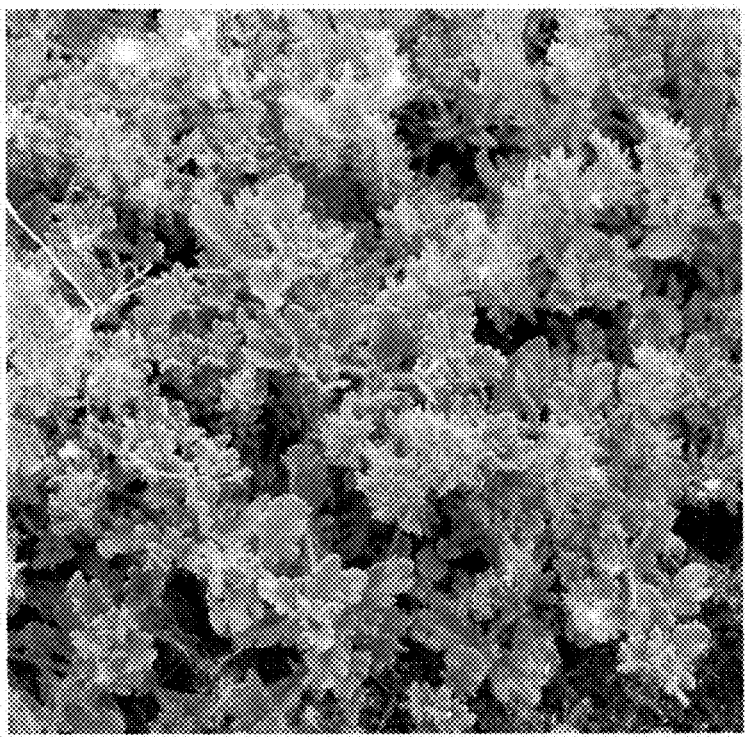

The photograph in FIG. 2 provides a close up view of the foliage of 'Tidal Pool'.

Figure 3:
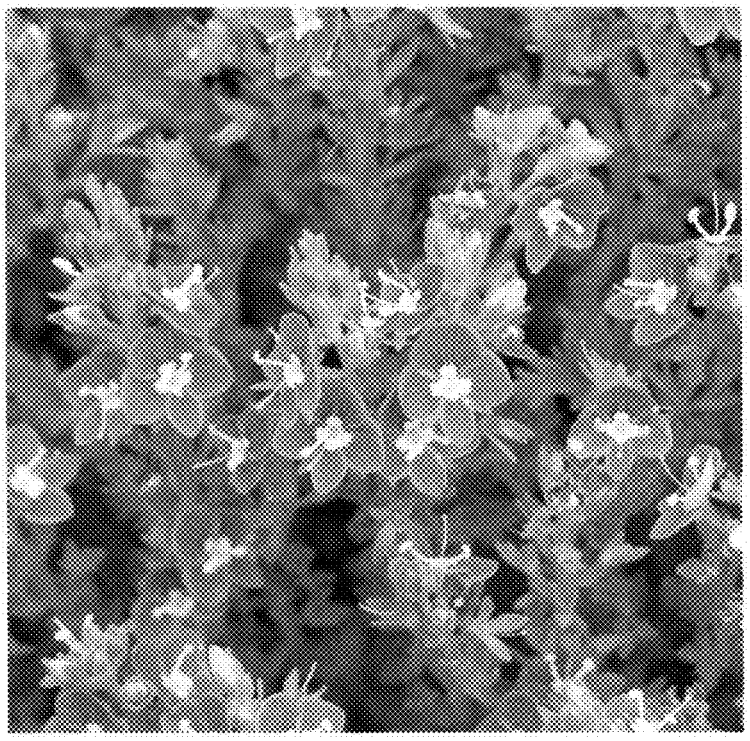

The photograph in FIG. 3 provides a close up view of the flowers of 'Tidal Pool'. The colors in the photograph may differ slightly from the color values cited in the detailed botanical description, which accurately describe the colors of the new *Veronica*.

DETAILED BOTANICAL DESCRIPTION

The following is a detailed description of the new cultivar as observed for a plant about 12-months in age as grown in a garden in New Hope, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—4 weeks from early to mid May until early to mid June with light repeat bloom from late June to September in Northern Illinois.

*Plant type*.—Perennial, evergreen with mild temperatures or good snow cover.

*Plant habit*.—Basal branching, prostrate plant habit, flowering stems emerging from axillary nodes, spreading groundcover.

*Height and spread*.—Reaches about 5 cm in height with a spread of about 56 cm when grown in alkaline clay soils and about 7.6 cm in height and 76 cm in spread when grown in sandy soils (2 year-old plant grown in Illinois).

*Hardiness*.—At least hardy in U.S.D.A. Zones 4 to 7.

*Diseases*.—Has shown resistance to leaf spot when grown among other *Veronica* that are infected.

*Root description*.—Fibrous.

*Propagation*.—Shoot tip cuttings.

*Growth rate*.—Vigorous.

Stem description:

*Shape*.—Round.

*Stem color*.—Young; 144D, mature; 144D and suffused with 185C.

*Stem size*.—Average of 2 mm in diameter and 20 cm in length.

*Stem surface*.—Pubescent.

*Branching habit*.—Abundant lateral branching.

Foliage description:

*Leaf division*.—Simple.

*Leaf arrangement*.—Opposite.

*Leaf shape*.—Obovate.

*Leaf size*.—An average of 1.2 cm in length and 1 cm length when mature.

*Leaf number*.—Average of 16 per stem 10 cm in length.

*Leaf base*.—Cuneate.

*Leaf apex*.—Broadly acute.

*Leaf margin*.—Shallowly lobed, 4 to 8 lobes per leaf, apices of lobes are broadly acute to rounded.

*Leaf venation*.—Pinnate, recessed on upper surface and raised on lower surface, color matches leaf color.

*Leaf surface*.—Sparsely pubescent on upper and lower surfaces.

*Leaf aspect*.—Held primarily horizontal to ground.

*Leaf internode length*.—An average of 1.2 cm.

*Leaf color*.—Newly formed and mature upper surface; 144A, newly formed and mature lower surface; 144B.

*Leaf attachment*.—Sessile.

Flower description:

*Inflorescence type*.—Racemes of rotate-shaped flowers from leaf axils.

*Lastingness of inflorescence*.—Individual flowers last 3 to 4 days, inflorescence lasts about 10 days, blooms from bottom of raceme towards apex.

*Inflorescence size*.—Racemes are about 7 cm in length and 1.8 cm in diameter.

*Flower type*.—Rotate.

*Flower number*.—About 22 flowers per raceme, an average of 2 racemes per stem.

*Flower fragrance*.—None.

*Flower buds*.—Elliptic in shape, about 5 mm in length and 3 mm in diameter, color 85B with calyx portion 138B.

*Flower size*.—About 5 mm in depth and 8 mm in diameter.

*Peduncles*.—About 7 cm in length and 1 mm in width, pubescent surface, color between 144A and 138B, flowers arranged in whorls, flower internode length an average of 3.5 mm.

*Pedicels*.—An average of 5 mm in length and 0.7 mm in width, pubescent surface, color between 144A and 138B, one leaf at the base of each petiole; about 4 mm in length and 1.5 mm in width, oblanceolate in shape with all other characteristics similar to leaf.

*Calyx*.—Campanulate becoming spreading when flower is fully open, about 4 mm in depth and width and becoming 1 mm in depth and 8 mm in width when spreading.

*Sepals*.—4, un-fused, about 1.5 mm in width and 4 mm in length, 138A in color, surface is glabrous on upper and lower surface, lanceolate in shape, acute-acuminate apex, tuncate base, entire margin.

*Petals*.—4, cordate in shape, broadly acute apex, fused at base to very short tube (0.8 mm in depth, 15 mm in width, and 145C in color), entire margin, color of upper surface a blend of 94A and 94B, color of lower surface a blend of 94D and 95D, up to 4 mm in length and 5 mm in width, glabrous and velvety surface.

Reproductive organs:

*Gynoecium*.—1 Pistil, style is about 4 mm in length, very fine and 155C in color, stigma is minute in size and 155C in color, ovary is superior, about 1 mm in diameter and 144A in color.

*Androecium*.—2 stamens, filament is about 3 mm in length, 0.4 mm in width and 155C in color, anthers are triangular in shape, about 0.8 mm in length, attachment is basifixed, and 158A in color, pollen is moderate in quantity and 11C in color.

*Fruit*.—Fruit and seed production was not observed under the conditions tested.

It is claimed:

1. A new and distinct variety of *Veronica* plant designated 'Tidal Pool' as described and illustrated herein.

* * * * *